United States Patent [19]
Knodel et al.

[11] Patent Number: 5,553,765
[45] Date of Patent: Sep. 10, 1996

[54] SURGICAL STAPLER WITH IMPROVED OPERATING LEVER MOUNTING ARRANGEMENT

[75] Inventors: Bryan D. Knodel, Cincinnati; Dale R. Schulze, Lebanon; Richard P. Nuchols, Loveland, all of Ohio

[73] Assignee: Ethicon Endo-Surgery, Inc., Cincinnati, Ohio

[21] Appl. No.: 431,105

[22] Filed: Apr. 28, 1995

[51] Int. Cl.⁶ .................................. A61B 17/068
[52] U.S. Cl. .............. 227/176.1; 227/19; 227/179.1
[58] Field of Search .............. 227/175.1, 176.1, 227/19, 178.1, 179.1

[56] References Cited

U.S. PATENT DOCUMENTS

| | | |
|---|---|---|
| Re. 34,519 | 1/1994 | Fox et al. . |
| 4,955,959 | 9/1990 | Tompkins et al. . |
| 5,040,715 | 8/1991 | Green et al. . |
| 5,084,057 | 1/1992 | Green et al. . |
| 5,100,420 | 3/1992 | Green et al. . |
| 5,129,570 | 7/1992 | Schulze et al. . |
| 5,307,976 | 5/1994 | Olson et al. . |
| 5,465,894 | 11/1995 | Clark et al. ............................ 227/19 |
| 5,465,895 | 11/1995 | Knodel et al. ........................ 227/19 |

*Primary Examiner*—Scott A. Smith
*Attorney, Agent, or Firm*—Dressler, Goldsmith, Milnamow & Katz, Ltd.

[57] ABSTRACT

A surgical instrument, illustrated as an endoscopic surgical stapler, includes first and second operating linkages respectively operatively connected with first and second operating levers pivotally mounted on a frame of the instrument. An improved mounting arrangement is provided for the operating levers in the form of first and second mounting bosses. The mounting bosses are formed separately in order to isolate forces exerted thereon by the operating levers attendant to use of the instrument.

8 Claims, 4 Drawing Sheets

SURGICAL STAPLER WITH IMPROVED OPERATING LEVER MOUNTING ARRANGEMENT

TECHNICAL FIELD

The present invention relates generally to surgical stapler instruments for applying rows of staples to tissue, while cutting the tissue between the rows of staples, and more particularly to an improved mounting arrangement for the operating levers of a surgical stapler.

BACKGROUND OF THE INVENTION

Surgical staplers greatly facilitate surgical procedures by permitting simultaneous application of rows of staples (in effect, suturing tissue) and cutting of tissue between adjacent rows of staples. Such devices typically include cooperating jaw members, one of which includes a staple-filled cartridge, and the other in the form of a staple anvil against which the staples are driven for deforming the legs of the staples, thereby effecting "suturing" of tissue positioned between the jaw members. Such staplers typically include one or more wedge-shaped cams which are operated to drive the staples against the anvil. When cutting of tissue is desired, these devices further include a tissue-cutting knife blade which is advanced between adjacent rows of staples.

Surgical staplers such as described above are disclosed in U.S. Pat. No. Re. 34,519, to Fox et al., U.S. Pat. No. 5,129,570, to Schulze et al., U.S. Pat. No. 4,955,959, to Tompkins, U.S. Pat. No. 5,040,715, to Green et al., and U.S. Pat. No. 5,307,976, to Olson et al., all of which are hereby incorporated by reference.

For endoscopic surgical procedures, an endoscopic surgical stapler such as disclosed in the above-referenced U.S. Pat. No. 5,307,976 can be employed. In such a device, the staple-filled cartridge and associated cooperating anvil are positioned at the distal end of a generally elongated endoscopic portion, which portion extends from a frame including a handle portion. The handle portion is grasped by the surgeon, with one or more operating levers, or like elements, provided at the handle portion for effecting the desired surgical steps. For example, in a typical construction, a first operating lever is operatively connected with the anvil of the stapler for moving the anvil toward the associated staple cartridge to grip and clamp tissue therebetween, with a second operating lever provided for thereafter driving the staples from the cartridge against the anvil.

Experience has shown that it can sometimes be difficult for a surgeon to judge the thickness of tissue being clamped between the staple cartridge and the anvil, and as a result, the forces generated in the operating levers and linkages of the stapler can vary. In some instances, relatively high forces can be created in the linkages and levers of the stapler, particularly in a construction such as disclosed in U.S. Pat. No. 5,040,715, wherein both of the operating levers of a surgical stapler are mounted on a common pivot pin. Also, it is often the case that the force to clamp tissue is significantly higher than the force to form staples and cut tissue, so the pivots of each of the operating levers need not be equally robust. However, it is desirable ergonomically to have the levers situated in the same area on the handle for the user to operate these levers more comfortably. In such a construction, the combined loads of both operating levers acting on a common pivot pin can create undesirably high stresses in tile pivot pin. The present invention is directed to an improved arrangement for mounting the operating levers on the associated frame of the stapler for accommodating the varying forces which can be encountered attendant to varying surgical conditions, while assuring precise and convenient control of the instrument by the surgeon.

SUMMARY OF THE INVENTION

In accordance with the present invention, a surgical instrument, illustrated in the form of an endoscopic surgical stapler, includes first and second operating linkages which are respectively operatively connected with first and second operating levers. The operating levers are respectively mounted on first and second mounting bosses, preferably formed integrally with a frame of the surgical stapler. The arrangement desirably acts to isolate the loads to which the mounting bosses are subjected attendant to pivotal movement of the respective operating levers. In the preferred embodiment, the first operating boss defines an annular bearing surface having an effective diameter which is greater than the effective diameter of an annular bearing surface of the second boss, thereby permitting carrying of relatively larger forces by the first mounting boss. This mounting boss is preferably employed for pivotal mounting of the lever which effects clamping of tissue, which surgical step may result in greater forces being generated within the instrument than the surgical step of driving the staples against the associated anvil.

In accordance with the illustrated embodiment, an endoscopic surgical stapler includes a frame including a handle portion configured to be held by a surgeon, and an elongated endoscopic portion joined to and extending from the frame. The endoscopic portion is insertable into a patient and is configured for effecting a plurality of surgical steps, in this case, clamping of tissue, and driving or firing of staples.

The present surgical stapler includes a staple-filled cartridge positioned at a distal end of the endoscopic portion, and an anvil positioned at the distal end of the endoscopic portion generally adjacent the cartridge. A first operating linkage is connected to the anvil for moving the anvil toward the cartridge to clamp tissue therebetween, i.e., a first surgical step. A second operating linkage includes staple driving cams for driving the staples out of the cartridge, and against the anvil, thus effecting a second surgical step.

In accordance with the present invention, a first mounting boss is provided integrally on the frame of the stapler, and defines a first generally annular bearing surface. A second mounting boss is also provided integrally on the frame of the stapler, with the second mounting boss defining a second generally annular bearing surface having an effective diameter substantially less than the effective diameter of the first bearing surface. In order to isolate loads to which the mounting bosses are subjected, the second mounting boss is positioned generally within and in spaced relationship to the first mounting boss. In the illustrated embodiment, the first bearing surface defines a first pivot axis, while a second bearing surface defines a second pivot axis coaxial with the first pivot axis but diametrically inwardly thereof. In this embodiment, the generally annular bearing surfaces are thus generally concentrically arranged, but axially offset from each other.

The endoscopic stapler includes first and second operating levers respectively operatively connected with the first and second operating linkages. The first and second operating levers are respectively pivotally mounted on the first and second mounting bosses.

In the preferred configuration, the first mounting boss has a C-shaped configuration, and defines a gap in the first bearing surface generally at a rearward portion thereof. The second mounting boss includes a support strut extending generally from the second bearing surface into the gap defined by the first mounting boss. The support strut desirably acts to reinforce and rigidify the second mounting boss, but does not interfere with free pivotal movement of the first operating lever carried on the C-shaped first mounting boss.

Other features and advantages of the present invention will become readily apparent from the following detailed description, the accompanying drawings, and the appended claims.

DETAILED DESCRIPTION

Figure 1:
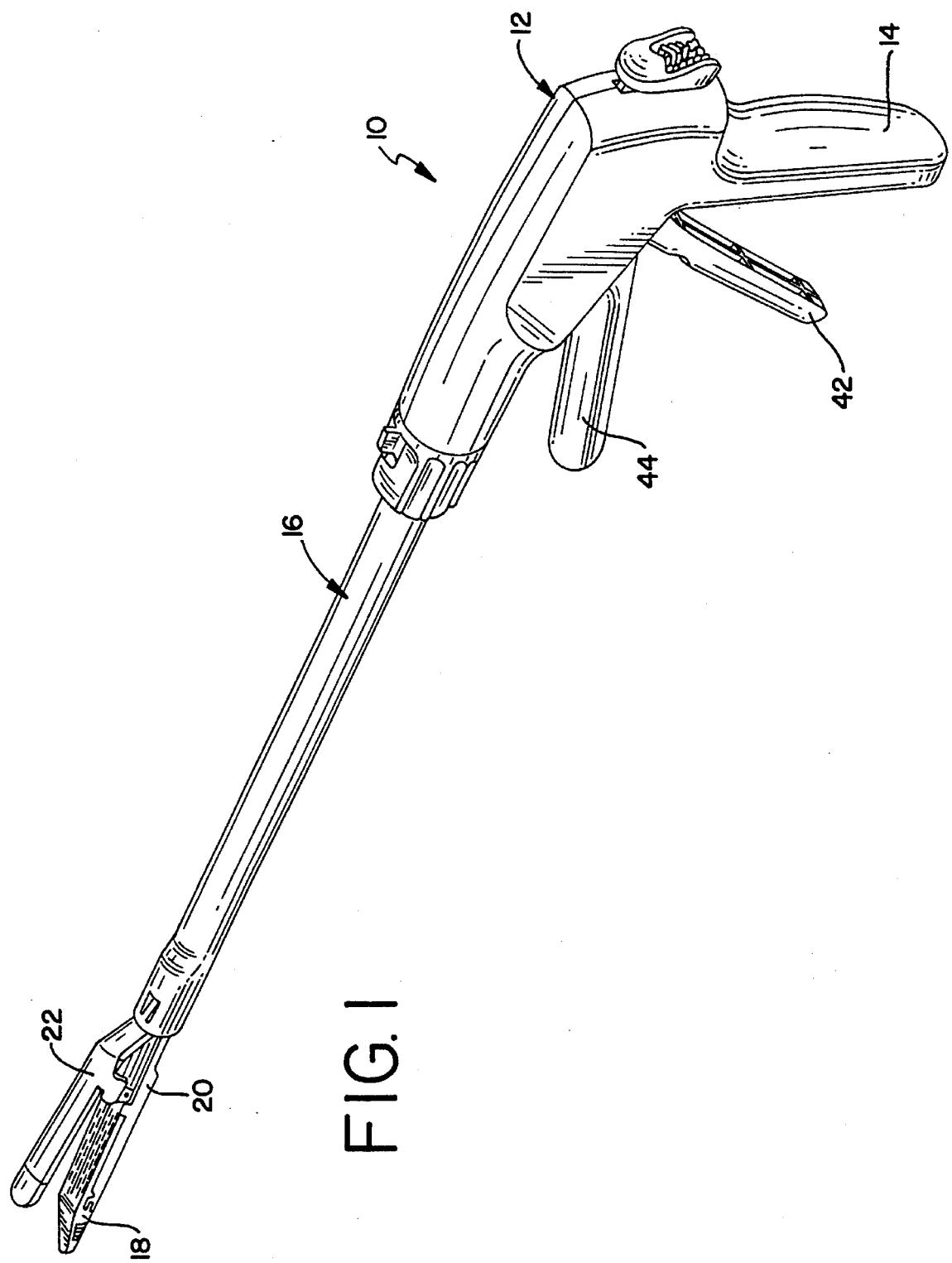
FIG. 1 is a perspective view of a surgical instrument, illustrated as an endoscopic surgical stapler, embodying the principles of the present invention.

While the present invention is susceptible of embodiment in various forms, there is shown in the drawings and will hereinafter be described a presently preferred embodiment, with the understanding that the present disclosure is to be considered as an exemplification of the invention, and is not intended to limit the invention to the specific embodiment illustrated.

With reference first to FIG. 1, therein is illustrated a surgical instrument, illustrated as an endoscopic surgical stapler 10, embodying the principles of the present invention. Endoscopic stapler 10 includes a frame 12 including a handle portion 14, and an elongated endoscopic portion 16 which is joined to and extends from the frame 12.

Stapler 10 further includes a pair of cooperating jaw members at the distal end of endoscopic portion 16, with a staple-filled cartridge 18 mounted in a jaw member 20, and with a cooperating jaw member provided in the form of a movable anvil 22 positioned for cooperation with cartridge 18 and jaw 20 to grip and clamp tissue between the anvil and the cartridge. The cartridge 18 contains a plurality of surgical staples which are deformed by driving the staples against the anvil 22, thereby "suturing" the tissue through which the staples are driven.

Figure 2:
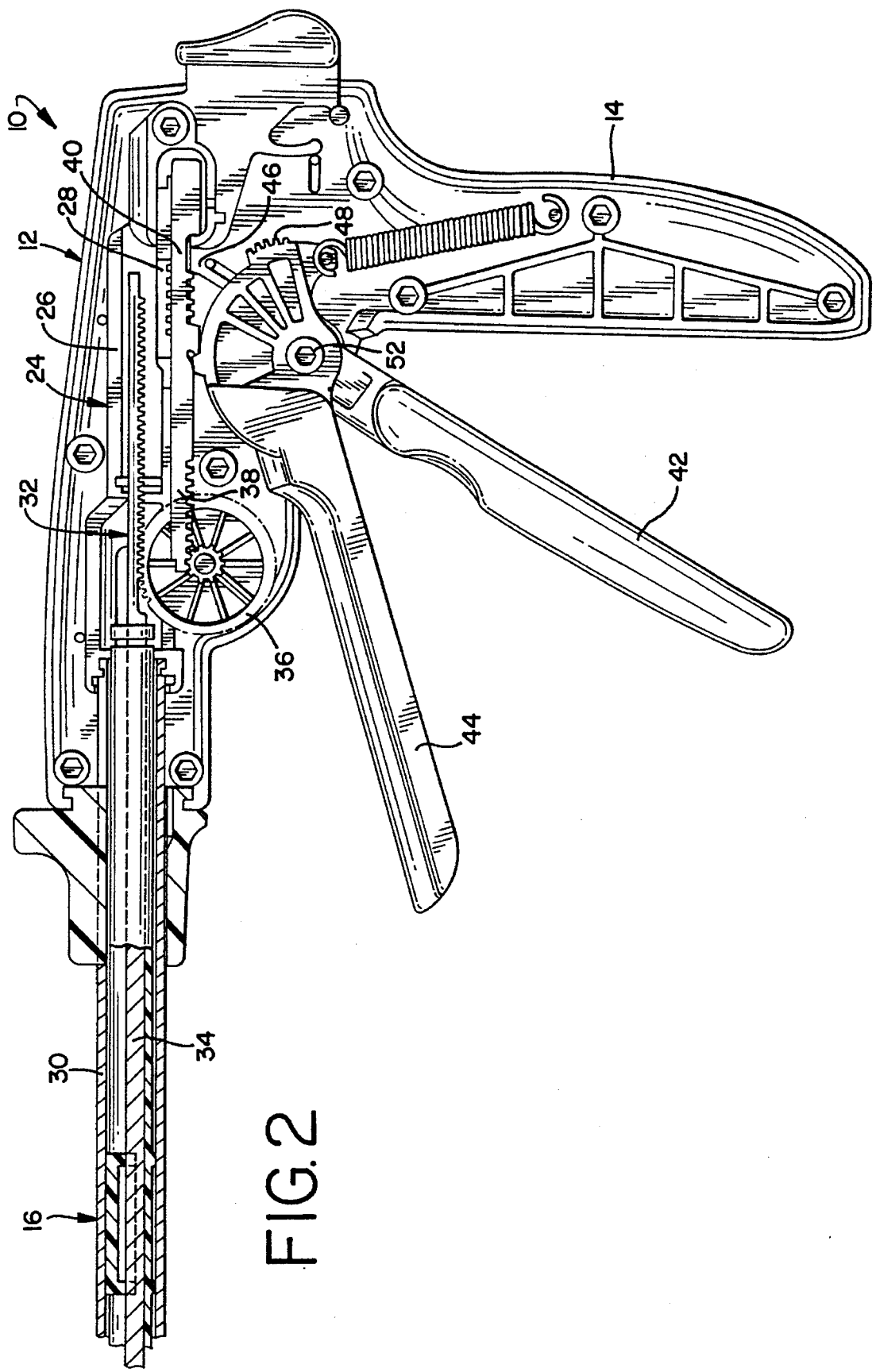
FIG. 2 is a partial cross-sectional view of the surgical stapler illustrated in FIG. 1.

A first operating linkage, :generally designated 24, is operatively connected to the anvil 22 for moving the anvil toward the cartridge 18 to clamp tissue therebetween. The first operating linkage 24 includes a reciprocable yoke 26 which is joined to an outer tubular portion 30 of endoscopic portion 16, and which has a first gear rack 28 (FIG. 2). Distal movement of tubular portion 30 against anvil 22 effects closing movement of the anvil as it is moved toward the staple-filled cartridge 18. Movement of the anvil for clamping tissue is the first surgical step performed during use of the present instrument.

A second operating linkage, generally designated 32, includes wedge-shaped driving caws (not shown) which move through staple-filled cartridge 18 for driving the staples therein against the anvil 22. The staple driving cams, which may be of a known and conventional configuration, are driven by an elongated reciprocable drive member 34 of the second operating linkage. The drive member 34, in ram, is driven by an idler gear 36, engaged with a gear rack on the drive member 34. Idler gear 36 of the second operating linkage is, in turn, driven by the generally elongated member 38 having a second gear rack thereon at 40. Movement of drive member 34 distally of endoscopic portion 16 acts to advance the wedge-shaped staple driving cams through staple cartridge 18 for driving or firing the staples therein.

Operation of the first and second operating linkages is respectively effected by first and second operating levers 42 and 44. As will be further described, first and second operating levers 42 and 44 are pivotally mounted on frame 12 of stapler 10, with the operating levers respectively operatively connected with the operating linkages by gear segments engageable with the gear racks of the linkages. Specifically, first operating lever 42 includes a first gear segment 46 (see FIG. 5) engageable with first gear rack 28 of the first operating linkage 24. Second operating lever 44 includes a second gear segment 48 (FIG. 2) enageable with second gear rack 40.

The illustrated embodiment of the present surgical stapler, including first and second operating linkages operated through gear racks and segments by first and second operating levers is further disclosed in copending U.S. patent application Ser. No. 08/191,412 filed Feb. 3, 1994, hereby incorporated by reference,. However, it is to be understood that a lever mounting arrangement, as further described hereinafter, can be employed in a surgical instrument other than configured in the drawings, and in the above-referenced application. Moreover, the lever-mounting arrangement can be readily employed in surgical instruments other than surgical staplers, wherein a plurality of surgical steps are effected by selected manipulation of first and second levers. For example, a mounting arrangement such as disclosed herein can be employed if desired in a surgical clip applier, such as disclosed in U.S. Pat. No. 5,084,057 and U.S. Pat. No. 5,100,420, hereby incorporated by reference.

The operation of surgical stapler 10 will be evident from the above description. Clamping of tissue between anvil 22 and staple-filled cartridge 18 is effected by manipulation and pivotal movement of first operating lever 42 generally toward handle portion 14 of frame 12. This pivotal movement acts through yoke 26 to move tubular portion 30 against anvil 22 for closing the anvil. Firing of staples can thereafter be effected by subsequent pivotal movement of second operating lever 44, which effects movement of drive member 34 through elongated member 38 and idler gear 36.

Figure 3:
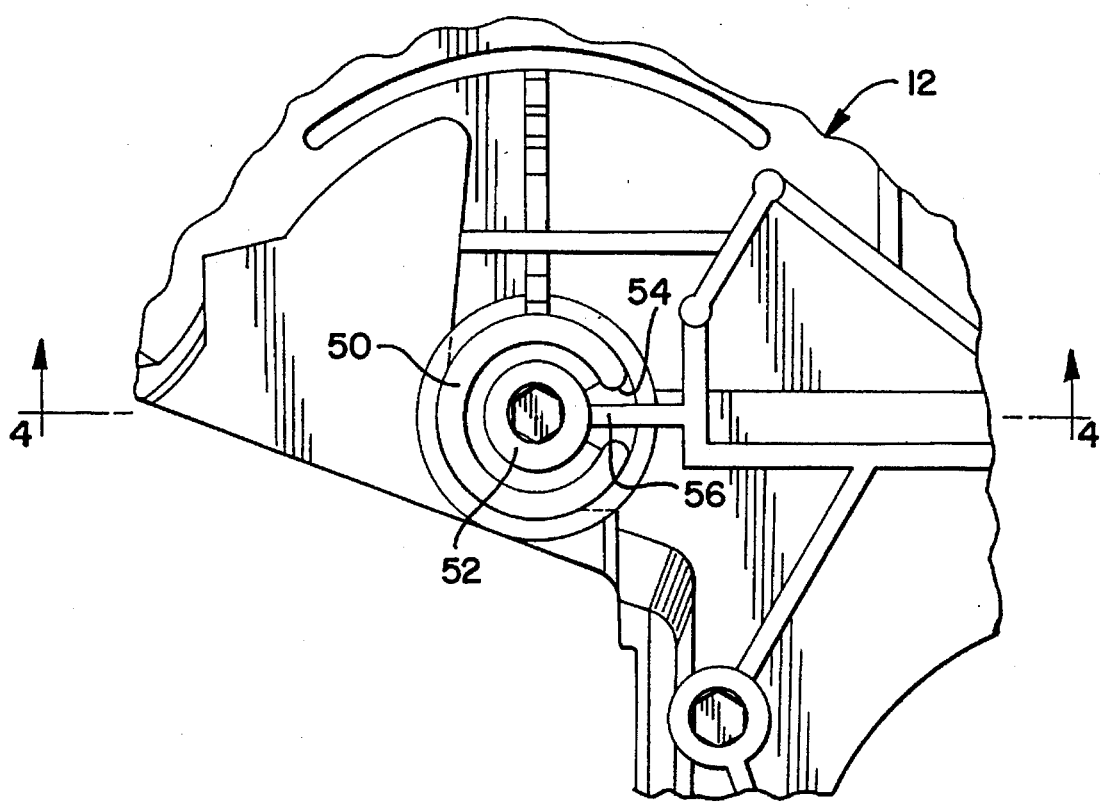
FIG. 3 is a fragmentary top plan view of a frame of the surgical instrument illustrated in FIGS. 1 and 2, illustrating the improved lever mounting arrangement of the present invention.
Figure 4:
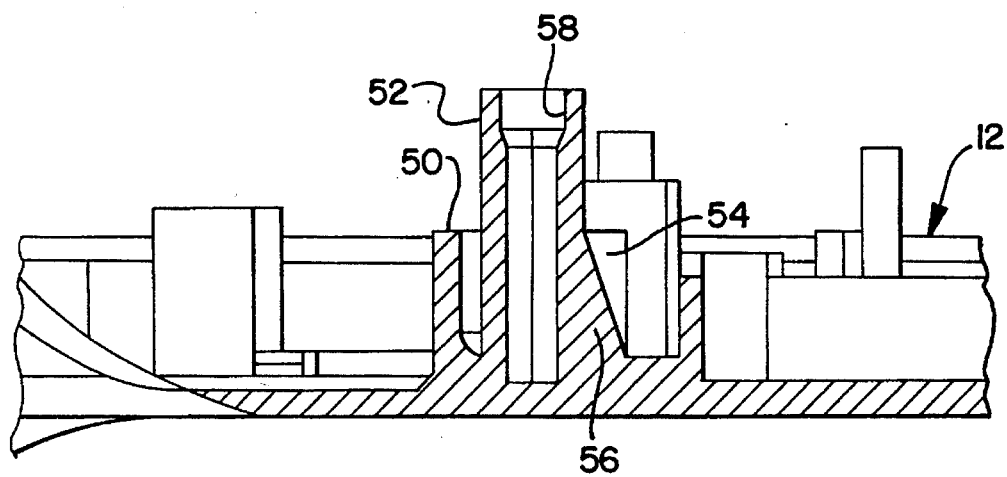
FIG. 4 is a cross-sectional view taken along lines 4—4 of FIG. 3.
Figure 5:
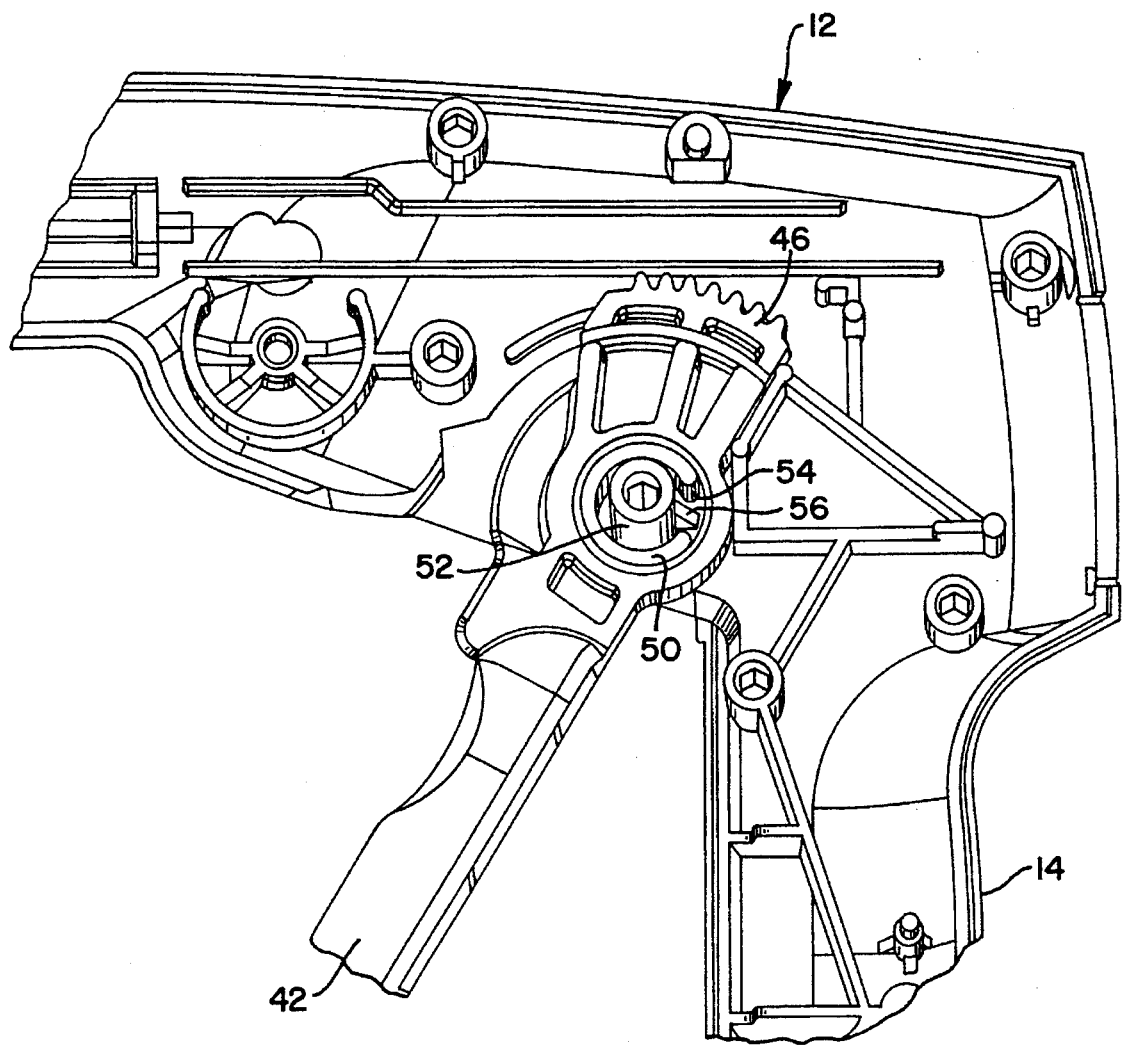
FIG. 5 is a fragmentary perspective view further illustrating the frame of the present surgical stapler, with an operating lever shown in position on the lever mounting arrangement thereof.

With particular reference to FIGS. 3–5, the lever mounting arrangement of the present invention will now be described. In particular, the lever mounting arrangement includes a first mounting boss 50 having a generally annular bearing surface upon which first lever 42 is pivotally mounted. The mounting arrangement further includes a second mounting boss 52, positioned generally within and spaced from first mounting boss 50, with the second operating lever 44 pivotally mounted on the second mounting boss.

As will be observed, the second mounting boss 52 has an annular bearing surface having an effective diameter substantially less than the effective diameter of the annular bearing surface of the first mounting boss 50. By virtue of the boss 50 having a larger diameter, and effective bearing surface, and since the boss 50 has a substantially larger base than boss 52 for attachment to frame 12, this mounting boss is capable of carrying relatively higher loads without undue stress, and thus mounting of first operating lever 42 (which operates to effect movement of anvil 22 for clamping tissue) is preferred.

Because forces generated attendant to movement of operating lever 42 toward handle portion 14 act generally against the forward portion of mounting boss 50, the mounting boss 50 need not be continuous. In the preferred illustrated embodiment, the annular bearing surface is discontinuous, and thus defines a gap 54 generally at the rear of the first mounting boss 50. In the present construction, the provision of the gap 54 is advantageously employed for the disposition of a support strut 56 of the second mounting boss 52. As best illustrated in FIG. 4, the support strut 56 extends generally from the annular bearing surface of the second boss 52 into the gap 54 defined by the first mounting boss. The support strut is thus positioned generally at the rear (i.e., proximally) of the second mounting boss 51. The support strut desirably acts to ridigify and reinforce the second mounting boss against bending moments exerted thereon, which result from the annular bearing surface thereof being spaced from the wall of frame 12 on which the mounting bosses are preferably integrally formed. Like first boss 50, second mounting boss 52 is ordinarily subjected to the greatest loads in a direction generally toward the rear (proximally) of the instrument as its operating lever is drawn toward handle portion 14. As a means of providing additional support for mounting boss 52, it is preferred that an integral pin member be provided extending into the interior 58 of boss 52 from the portion of frame 12 opposite that portion on which bosses 50, 52 are integrally formed.

As shown in FIGS. 3 and 4, the first and second mounting bosses 50, 52 respectively define first and second pivot axes, which preferably are coaxial. Thus, the annular bearing surfaces of the mounting bosses are generally concentrically arranged, but are axially offset from each other. In the illustrated embodiment, the bearing surface of first mounting boss 50 has an axial dimension approximately equal to an axial dimension of the bearing surface of second boss 52, with the effective bearing surface area of the first boss being substantially greater than that of the second boss by virtue of the greater effective diameter of the first mounting boss. Additionally, the preferred disposition of the bearing surface of first boss 50 closer to the wall of frame 12 than the bearing surface of second boss 52 desirably acts to reduce the bending moments to which the first boss is subjected.

From the foregoing, it will be observed that numerous modifications and variations can be effected without departing from the true spirit and scope of the novel concept of the present invention. It is to be understood that the present disclosure is to be considered as an exemplification of the invention, and is not intended to limit the invention to the specific embodiment illustrated. The disclosure is intended to cover, by the appended claims, all such modifications as fall within the scope of the claims.

What is claimed is:

1. An endoscopic surgical stapler, comprising:

a frame including a handle portion configured to be held by a surgeon;

an elongated endoscopic portion joined to an extending from said frame, said endoscopic portion being insertable into a patient for effecting a plurality of surgical steps;

a staple cartridge portion at a distal end of said endoscopic portion, said cartridge containing a plurality of surgical staples;

an anvil positioned at said distal end of said endoscopic portion generally adjacent said staple cartridge;

a first operating linkage connected to said anvil for moving said anvil toward said cartridge to clamp tissue between said anvil and said cartridge;

a second operating linkabe for driving said staples out of said cartridge, and against said anvil for deforming said staples;

a first mounting boss on said frame defining a first generally annular bearing surface, and a second mounting boss on said frame defining a second generally annular bearing surface having an effective diameter substantially less than an effective diameter of said first bearing surface, said second mounting boss being positioned generally within and in spaced relationship to said first mounting boss, said first mounting boss having a C-shaped configuration defining a gap in the first bearing surface generally at a rearward portion thereof, said second mounting boss including a support strut extending generally from said second bearing surface into said gap defined by said first mounting boss; and first and second operating levers respectively operatively connected with said first and second operating linkages, and respectively pivotally mounted on said first and second mounting bosses.

2. An endoscopic surgical stapler in accordance with claim 1, wherein said first annular bearing: surface has an axial dimension approximately equal to an axial dimension of said second annular bearing surface.

3. An endoscopic surgical stapler in accordance with claim 1, wherein said first bearing surface defines a first pivot axis, and said second bearing surface defines a second pivot axis coaxial with said first pivot axis, said first and second bearing surfaces being axially offset from each other.

4. An endoscopic surgical stapler in accordance with claim 1, wherein said first and second operating linkages respectively include first and second gear racks, each of said first and second operating levers including a gear segment respectively engageable with said first and second gear racks for respectively operatively connecting said first and second operating levers with said first and second operating linkages.

5. A surgical instrument, comprising:

a frame including a handle portion;

a portion joined to and extending from said frame for effecting a plurality of surgical steps;

a first operating linkage for effecting a first surgical step;

a second operating linkage for effecting a second surgical step;

a first mounting boss on said frame defining a first generally annular bearing surface, and a second mounting boss on said frame defining a second generally annular bearing surface axially spaced from and having an effective diameter substantially less than an effective diameter of said first bearing surface, said second mounting boss being positioned generally within and in spaced relationship to said first mounting boss, said first annular bearing surface being positioned closer to a wall of said frame than said second annular bearing surface; and first and second operating levers respectively operatively connected with said first and second operating linkages, and respectively pivotally mounted on said first and second mounting bosses.

6. A surgical instrument in accordance with claim 5, wherein said first mounting boss has a C-shaped configuration defining a gap in the first bearing surface generally at a rearward portion thereof;

said second mounting boss being positioned generally within said first mounting boss and including a support strut extending generally from said second bearing surface into said gap defined by said first mounting boss.

7. A surgical instrument in accordance with claim 5, wherein said instrument comprises a stapler, and includes a staple-filled cartridge positioned at a distal end of said portion, and an anvil positioned generally adjacent said cartridge, said first operating linkage for effecting said first surgical step being connected to said anvil for moving said anvil toward said cartridge to clamp tissue therebetween, and said second operating linkage for effecting said second surgical step including staple driving means for driving staples out of said cartridge and against said anvil.

8. A surgical instrument in accordance with claim 5, wherein said first annular bearing surface has an effective bearing surface area greater than an effective bearing surface area of said second annular bearing surface.

* * * * *